United States Patent [19]

Mendiratta et al.

[11] 4,025,545

[45] May 24, 1977

[54] HYDROGEN HALIDE REMOVAL IN HALOGENATED ALIPHATIC NITRILE PRODUCTION

[75] Inventors: Sudhir K. Mendiratta; Ronald L. Dotson; George M. Shipley, all of Cleveland, Tenn.

[73] Assignee: Olin Corporation, New Haven, Conn.

[22] Filed: Feb. 25, 1976

[21] Appl. No.: 661,404

[52] U.S. Cl. .......................................... 260/465.7
[51] Int. Cl.$^2$ ..................................... C07C 121/14
[58] Field of Search ................................ 260/465.7

[56] References Cited

UNITED STATES PATENTS

| | | | |
|---|---|---|---|
| 2,283,237 | 5/1942 | Spence et al. | 260/465.7 |
| 2,375,545 | 5/1945 | Foster | 260/465.7 |
| 2,443,494 | 6/1948 | Cass | 260/465.7 X |
| 2,463,629 | 3/1949 | Karr | 203/52 |

FOREIGN PATENTS OR APPLICATIONS

| | | | |
|---|---|---|---|
| 522,835 | 6/1940 | United Kingdom | 260/465.7 |
| 750,712 | 6/1956 | United Kingdom | 260/465.7 |

*Primary Examiner*—Joseph Paul Brust
*Attorney, Agent, or Firm*—William A. Simons; Thomas P. O'Day; F. A. Iskander

[57] ABSTRACT

Hydrogen halide levels of halogenated aliphatic nitriles are unexpectedly reduced by condensing a vapor comprising hydrogen halide and halogenated aliphatic nitrile at selected elevated temperatures, thus producing a product having reduced hydrogen halide levels and improved storage stability.

8 Claims, 1 Drawing Figure

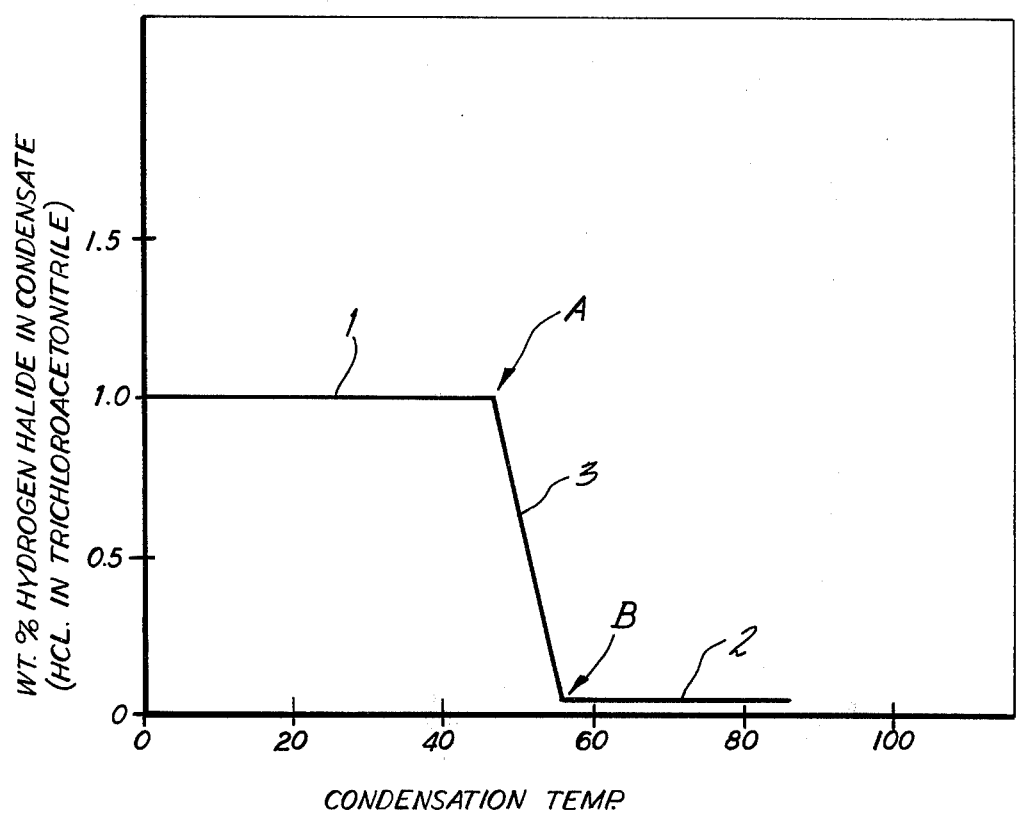

HYDROGEN HALIDE REMOVAL IN HALOGENATED ALIPHATIC NITRILE PRODUCTION

BACKGROUND OF THE INVENTION

1. Field of Invention

The present invention relates to the preparation of halogenated aliphatic nitriles and in particluar to preparation of halogenated aliphatic nitriles by halogenating an aliphatic nitrile in the presence of a halogenation catalyst or initiator. More particularly, the invention relates to a method for removing hydrogen halide from a mixture of a hydrogen halide and a halogenated aliphatic nitrile in order to produce a product having low hydrogen halide content and improved storage stability.

2. Prior Art

Halogenated aliphatic nitrilies are generally prepared commerically by direct halogenation of an aliphatic nitrile or of a less completely halogenated aliphatic nitrile. The halogenation may be conducted as a liquid phase halogenation, a vapor phase halogenation or a liquid phase halogenation utilizing a gaseous halogenating agent. Reaction conditions disclosed in the art vary widely as to temperature, procedural steps, catalysts employed, halogenating agents employed and other reaction parameters.

Likewise, numerous means have been set forth for separating by-products and unreacted reactants. In liquid phase halogenations, hydrogen halide has been partially separated by heating with or without stripping gases to degas the reaction mixture and/or by a series of distillations in the presence of various solvents. An example of this is set forth in A. Karr, U.S. Pat. 2,463,629 wherein azeotropic distillation is employed.

Another means which has been used with both liquid and vapor phase reactions is to contact the reaction mixture, in liquid form, with water to remove water solubles, separate phases, dry the organic phase with a suitable drying agent such as calcium chloride then purify the organic phase by distillation. An example of this procedure and modifications thereof are shown in R. T. Foster, U.S. Pat. No. 2,375,545 and L. U. Spence, U.S. Pat. No 2,283,237.

It is known, as shown in British Patent 522,835, that the presence of hydrogen halides, at least during the halogenation reaction, leads to the formation of excess residues. In the case of trichloroacetonitrile, these residues are principally triazines and polymeric derivatives thereof. We have found that the presence of small amounts of hydrogen halides in the final halogenated aliphatic nitrile product will lead to this type of residue formation upon prolonged storage, that rapid residue formation occurs if a halogenated aliphatic nitrile, contaminated with more than minor amounts of hydrogen halide, is stored in the presence of transition metal compounds, particularly in the presence of ferric ion, but that this degradation is significantly reduced when the hydrogen halide concentration is reduced below that normally found bound to the nitrile when recovered according to presently known processes.

Prior processes for preparing halogenated aliphatic nitriles, at some point in the processing cycle, generate hydrogen halide in amounts greater than that acceptable to produce a storage stable product. One known means for attempting to remove hydrogen halide from an halogenated aliphatic nitrile mixture is to heat the mixture to a temperature approaching the boiling point and strip the hydrogen halides off by known means, remove the gases and then utilize only the liquid phase as final product. The gas phase is condensed at low temperatures and either neutralized and discarded or recycled to the process. The problem with this procedure is that at temperatures utilized to degas the mixture, substantial amounts of the nitrile are also removed. Condensation techniques heretofore employed do not permit recovery thereof substantially free of the hydrogen halide.

Another separation procedure which has been employed is to distill the entire reaction mixture containing halogenated aliphatic nitrile and hydrogen halide, leaving only residues behind, and then condense the resulting vapors at low temperatures. This technique produces a condensate having higher levels of hydrogen halide than those acceptable for a storage stable product.

We have now found that when a reaction mixture containing a halogenated aliphatic nitrile and hydrogen halide is heated above what shall be hereinafter referred to as a second predetermined temperature, a vapor is provided in which the nitrile and hydrogen halide exist in uncombined or unassociated form, that when the resulting vapor is then condensed at a temperature above what shall be hereinafter referred to as a first predetermined temperature which is below the boiling point of the halogenated aliphatic nitrile is obtained as a condensate which has unexpectedly reduced amounts of hydrogen halide and significantly improved storage stability. However, if condensation is effected at a temperature below the first predetermined temperature, a nitrile product is formed which contains unacceptably high levels of hydrogen halide and which has limited storage stability. As used herein, all references to condensation temperature refer to the condensate temperature at the time condensate is separated from the gas phase, i.e., removed from the condenser.

SUMMARY OF THE INVENTION

In accordance therewith the present invention provides a method for more completely separating a hydrogen halide from a mixture of hydrogen halide and halogenated aliphatic nitrile which comprises heating the mixture to a temperature above the second predetermined temperature, thus vaporizing the hydrogen halide and at least a portion of the halogenated aliphatic nitrile and forming a vapor in which the two exist in unassociated form, then partially cooling the resulting vapors and condensing the same at a condensation temperature above the first predetermined temperature. In the preferred embodiment, condensation is conducted at a temperature about equal to the second predetermind temperature but below vaporization temperature.

DETAILED DESCRIPTION

The accompanying drawing is a diagram showing the relationship between concentration of hydrogen halide in a halogenated aliphatic nitrile condensed at different condensation temperatures within the range of 0° C. up to about 80° C. in the presence of gaseous hydrogen chloride. It is to be noted that the amount of hydrogen chloride found in the condensate does not vary at a constant rate depending on the condensation temperature as one would expect from the usual rules governing gas/liquid equilibria, but unexpectedly shows 2 sharp fluctuations, A and B, over this temperature range.

If condensed below the temperature represented by point A, about 44° C. in the case of a trichloroacetonitrile/hydrogen chloride mixture, the amount of hydrogen chloride in the condensate remains relatively constant regardless of temperature as shown in line segment 1. If the mixture is heated above the temperature represented by point B or the mixture itself vaporized and the vapor then condensed at a temperature below 44° C., the amount of hydrogen chloride present in the condensation will return to its original value, i.e., the value represented by line segment 1 of the drawing. This amount is sufficient to adversely affect storage stability of the product.

If, on the other hand, the mixture is heated above the temperature represented by point B and hydrogen chloride or the mxiture itself vaporized and then condensed at a temperature above that at point B, the HCl1 content of the resulting condensate is reduced to a value approaching zero at which storage stability of the resulting trichloroacetonitrile is substantially improved. This value is again relatively constant above the temperature represented by point B but below the boiling point of the nitrile as shown by line segment 2.

If condensation is conducted at a temperature between the first predetermined temperature (A) and the second predetermined temperature (B), the amounts of hydrogen halide in the resulting condensate decreases dramatically for each incremental increase in condensation temperature (and vice versa) as shown by line segment 3 of the drawing.

This unique behavior is applicable to all halogenated aliphatic nitriles in the presence of hydrogen halides, with the respective points A and B being different for each nitrile. The reasons for this behavior has not yet been firmly established but, without being bound by any particular theory, we believe that the halogenated aliphatic nitrile and hydrogen halide have a relationship such that below the first predetermined temperature (A), the nitrile and at least a portion of the hydrogen halide are associated in solution in combined form. It is believed that there exists at this temperature a stable adduct between the two does not begin to dissociate until the first predetermined temperature (A) has been exceeded. When the first predetermined temperature is exceeded that portion of the hydrogen halide which was in bound form dissociates over a relatively narrow temperature range up to the second predetermined temperature (B) at or above which the association is substantially destroyed.

For any given halogenated aliphatic nitrile and/or hydrogen halide, the first and second predetermined temperatures (A and B respectively) described above may be established most conveniently by distilling a mixture of halogenated aliphatic nitrile and hydrogen halide, condensing at various elevated temperatures below the boiling point of the nitrile, removing condensate samples at each temperature, titrating each sample by a standard non-aqueous titration with caustic and by plotting HCl concentration of the condensate against condensation temperature as shown in the drawing. In each instance both predetermined temperatures are elevated above normal ambient temperature, i.e., 20° C.–30° C. Thus, in all instances, condensation is, in accordance with the present invention, effected at elevated temperature in order to avoid adduct formation upon condensation of the halogenated aliphatic nitrile.

Thus, in accordance with this invention, a mixture of the halogenated nitrile and hydrogen halide is heated above the second predetermined temperature (B), at which temperature the association therebetween is substantially destroyed. This provides a vapor comprising the nitrile and the halide in unassociated form. Preferably, one may vaporize at a temperature which is above the boiling point of the nitrile, distill the mixture and leave behind only residues. The upper vaporization temperature limit is dictated by practical considerations, while the lower limit corresponds to the second predetermined temperature if adequate hydrogen halide removal is to occur.

Following vaporization at a temperature equal to or greater than the second predetermined temperature, the vapors partially cooled and are condensed in any known manner at a condensation temperature above the first predetermined temperature but below the boiling point of the halogenated nitrile and, obviously, below the vaporization temperature. Preferably, the condensation temperature is approximately the same as the second predetermined temperature plus or minus about five centigrade degrees. By operating at or about this temperature, one may approach maximum hydrogen halide separation, and simultaneously maximize thermal efficiency of the process.

It is preferred that the condensation be conducted at atmospheric pressure but any suitable pressure, for example, from 0.1–10 atmospheres may be employed, if desired, with the recognition that the respective points A and B wil vary with the pressure employed.

Substrates for which the present invention may be utilized includes a mixture of hydrogen halide in halogenated aliphatic nitrile, advantageously a halogenated saturated aliphatic nitrile, preferably a halogenated saturated lower aliphatic nitrile having 2–4 carbon atoms and most preferably a halogenated acetonitrile such as trichloroacetonitrile.

The halogen substituent may suitably be chlorine or bromine or both with the number of halogen substituents being from 1 up to the number of hydrogens available for substitution. The hydrogen halide may be present in any amount in the starting mixture.

Thus, suitable substrates would include, for example, hydrogen chloride in combination with mono-, di- or trichloroacetonitrile or any mixture thereof, hydrogen bromide in combination with mono-, di- or tribromoacetonitrile or any mixture thereof, or hydrogen bromide or a mixture thereof in combination with mono- or dichloromonobromoacetonitrile or mono- or dibromomonochloroacetonitrile. The preferred mixture comprises trichloroacetonitrile contaminated with hydrogen chloride.

With respect to trichloroacetonitrile which is contaminated with hydrogen chloride, the mixture is heated at least to a temperature of 58° C.–63° C., corresponding to the second predetermined temperature, and may be heated to any desired temperature thereabove in order to remove the hydrogen halide along with at least a portion of the trichloroacetonitrile. If it is desired to remove little trichloroacetonitrile with the hydrogen chloride vapors, the vaporization temperature utilized should be in the range of 58° C. to about 85° C., i.e., above the second predetermined temperature to provide a vapor containing the hydrogen halide and the nitrile in unassociated form, but below the boiling point of the nitrile. If it is desired to remove all but residues, substantially higher temperature must be employed, for example, from about 85° C. up to about 150° C.

The vapor thus produced is then partially cooled and condensed at elevated temperature in a suitable condenser, condensation temperature being above the first predetermined temperature (which for a hydrogen chloride/trichloroacetonitrile mixture is about 43° C.–48° C.) but below the boiling point of trichloroacetonitrile, i.e., ~85° C. Preferably, condensation is conducted at or about the second predetermined temperature to optimize thermal efficiency and minimize hydrogen chloride in the condensate.

The resulting product has an HCl concentration of not more than about 0.4 wt. %, advantageously less than 0.3 wt.%, preferably less than 0.25 wt. %.

The condensation may be conducted in any known manner utilizing the temperatures specified and may be conducted in a single or as a series of condensations at different temperatures within the limits specified above, this aspect being within the skill of the art.

The following examples demonstrate the practice of the present invention utilizing a mixture containing hydrogen chloride in trichloroacetonitrile formed by liquid phase chlorination of acetonitrile in the presence of hydrogen chloride. Excess hydrogen chloride may also be present but does not significantly alter the results shown. The uncondensed hydrogen chloride may be neutralized and sewered, recycled to the process or sold as industrial grade hydrochloric acid. All percentages are expressed as weight percentages unless it is expressly stated to the contrary.

EXAMPLE 1

Trichloroacetonitrile containing 0.9% HCl was fed to a distillation flask maintained at the boiling point of the mixture, i.e., about 85° C. and was vaporized until only tarry residues remained. The resulting vapors were collected in a condenser and condensed, the temperature of the condenser being controlled such that the temperature of the collected condensate, when removed, was as reported in Table I. HCl content of each sample recovered was measured by non-aqueous titration with caustic and is reported in Table I.

TABLE I

| Sample | Condensation Temp. (° C.) | HCl Concentration (wt. %) |
| --- | --- | --- |
| 1.1 | 75 | 0.15 – 0.25 |
| 1.2 | 60 | 0.15 – 0.25 |
| 1.3 | 50 | 0.4 |
| 1.4 | 40 | 0.9 |
| 1.5 | 22 | 0.9 |

EXAMPLE 2

The trichloroacetonitrile mixture of Example 1 was heated to these same temperatures under violent agitation while passing a stripping gas through each sample. Each sample was held at the specified temperature for about 30 minutes. The reaction mixture was then cooled, filtered and HCl content measured by non-aqueous titration with caustic. HCl values are reported in Table II.

TABLE II

| Sample | Solution Temp. (° C.) | HCl Concentration (wt. %) |
| --- | --- | --- |
| 2.1 | 75 | 0.3 |
| 2.2 | 60 | 0.5 |
| 2.3 | 50 | 0.6 |
| 2.4 | 40 | 0.9 |

TABLE II-continued

| Sample | Solution Temp. (° C.) | HCl Concentration (wt. %) |
| --- | --- | --- |
| 2.5 | 22 | 0.9 |

This example demonstrates that for any given temperature below the boiling point of the resulting nitrile hydrogen halide removal by a degassing technique results in a solution having a higher hydrogen halide concentration except where the degassing temperature is below that presented by point A above.

EXAMPLE 3

Trichloroacetonitrile samples having the amounts of hydrogen chloride (wt. %) shown below were studied to determine the effect of impurities such as acetonitrile, metallic iron, water and ferric chloride. The samples were placed in glass bottles and mixed with various impurities and the rate of residue build up followed for 14 weeks. Degradation rates (wt. %/ week triazine formation) of the respective samples are shown below the various impurities.

TABLE III

| Sample | HCl Conc. | Other Impurity | Level | Degradation Rate |
| --- | --- | --- | --- | --- |
| 2.1 | 0.3 | Acetonitrile | 5% | ~0.05 |
| 2.2 | 0.3 | Metallic Iron | Excess | ~0.05 |
| 2.3 | 0.3 | Water | 0.1% | ~0.05 |
| 2.4 | 0.8 | — | — | ~0.5 |
| 2.5 | 0.4 | $FeCl_3$ | 100 ppm $Fe^{+3}$ | 3.5 |
| 2.6 | 0.2 | $FeCl_3$ | 100 ppm $Fe^{+3}$ | ~0.05 |

We claim:

1. A method for removing hydrogen halide from a mixture of said hydrogen halide and a halogenated saturated aliphatic nitrile, said halide and halogen substituents being selected from the group consisting of chlorine, bromine, or both, and said hydrogen halide and said nitrile having a relationship such that below a first predetermined temperature said nitrile and at least a portion of said hydrogen halide are associated in combined form in said mixture and such that at or above a second predetermined temperature above said first temperature said association is substantially destroyed, which comprises:
   1. Heating said mixture at a temperature equal or greater than said second predetermined temperature to provide a vapor comprising said hydrogen halide and at least a portion of said halogenated aliphatic nitrile in substantially unassociated form.
   2. Condensing said vapor at a condensation temperature above said first temperature but below the boiling point of said nitrile, recovering said nitrile as a condensate having levels of said hydrogen halide.
2. The process of claim 1 wherein said nitrile is trichloroacetonitrile and said hydrogen halide is hydrogen chloride.
3. The process of claim 2 wherein said first temperature is in the range of 43° C.–48 ° C. and said second temperature is in the range of 58° C.–63° C.
4. The process of claim 3 wherein said vapor is condensed at a temperature between 58° C.–85° C.
5. The process of claim 4 wherein said vapor is condensed at atmospheric pressure.
6. The process of claim 4 wherein said vapor is condensed at a temperature in the range of 58° C.–63° C.
7. The process of claim 6 wherein said vapor is condensed at atmospheric pressure.
8. The process of claim 1 wherein said satuated aliphatic nitrile is a saturated lower aliphatic nitrile having 4–6 carbon atoms.

* * * * *

UNITED STATES PATENT OFFICE
CERTIFICATE OF CORRECTION

Patent No. 4,025,545     Dated May 24, 1977

Inventor(s) Sudhir K. Mendiratta, Ronald L. Dotson and George M. Shipley

It is certified that error appears in the above-identified patent and that said Letters Patent are hereby corrected as shown below:

Column 2, line 29, before the word "halogenated" insert --nitrile, the--.

Column 3, line 20, "HCll" should read --HCl--.

Column 3, line 44, after the word "two" insert --which--.

Column 4, line 6, before the word "halide" insert --hydrogen--.

Column 4, line 31, "wil" should be spelled --will--.

Column 4, line 68, "temperature" should read --temperatures--.

Column 6, line 51, after the word "having" insert --reduced--.

Column 6, line 65, "satuated" should be spelled --saturated--.

Column 6, line 67, "4-6" should read --2-4--.

Signed and Sealed this

Twenty-ninth Day of November 1977

[SEAL]

Attest:

RUTH C. MASON  
Attesting Officer

LUTRELLE F. PARKER  
Acting Commissioner of Patents and Trademarks